United States Patent [19]

Hosli

[11] 4,162,896
[45] Jul. 31, 1979

[54] MICRO-ANALYSIS PROCESS AND DEVICE

[75] Inventor: Peter Hösli, Paris, France

[73] Assignee: Institut Pasteur, Paris, France

[21] Appl. No.: 881,354

[22] Filed: Feb. 27, 1978

[30] Foreign Application Priority Data

Mar. 9, 1977 [FR] France ............................... 77 07016

[51] Int. Cl.² ........................... B01L 3/00; G01N 1/10
[52] U.S. Cl. ............................... 23/230 R; 23/230 B;
73/425.4 P; 422/100; 422/102; 422/104;
435/30; 435/292; 435/293
[58] Field of Search ..... 23/230 R, 230 B (U.S. only),
23/253 R, 259, 292; 73/425.4 P; 195/103.5 R,
120, 127; 422/99, 100, 102, 104

[56] References Cited

U.S. PATENT DOCUMENTS

| 3,048,999 | 8/1962 | Pochan | 23/292 X |
| 3,252,331 | 5/1966 | Lancaster | 73/425.4 P |
| 3,479,881 | 11/1969 | Unger | 73/425.4 P |
| 3,641,823 | 2/1972 | Harris, Sr. et al. | 73/425.4 P |
| 3,757,584 | 9/1973 | Gallant | 23/292 X |
| 3,876,376 | 4/1975 | Bauman et al. | 23/259 X |
| 3,901,085 | 8/1975 | Faure | 73/425.4 P |
| 3,932,136 | 1/1976 | Stickney | 23/253 R X |
| 4,040,234 | 8/1977 | Stockdale et al. | 23/292 X |

Primary Examiner—Joseph Scovronek
Attorney, Agent, or Firm—Weiser, Stapler & Spivak

[57] ABSTRACT

The invention relates to novel processes and devices for the analysis of samples of very small volume.

The process consists in taking definite amounts of reagents by capillarity on the end of fine rods, then recovering the amounts taken by centrifugation, the reagents being projected to the bottom of the same container. The device comprises elements for taking up, associated with a container able to be centrifuged.

The process and the device are particularly useful for enzymatic micro-analyses.

28 Claims, 10 Drawing Figures

Fig.1. Fig.2. Fig.3. Fig.4. Fig.5.
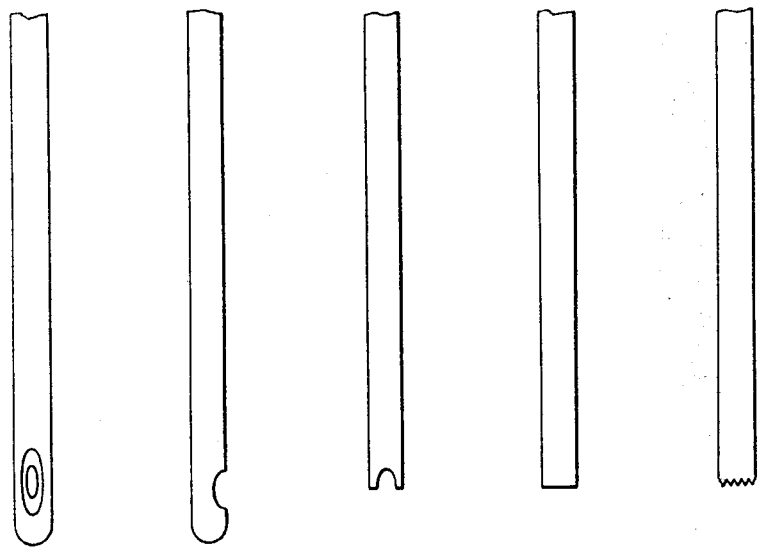
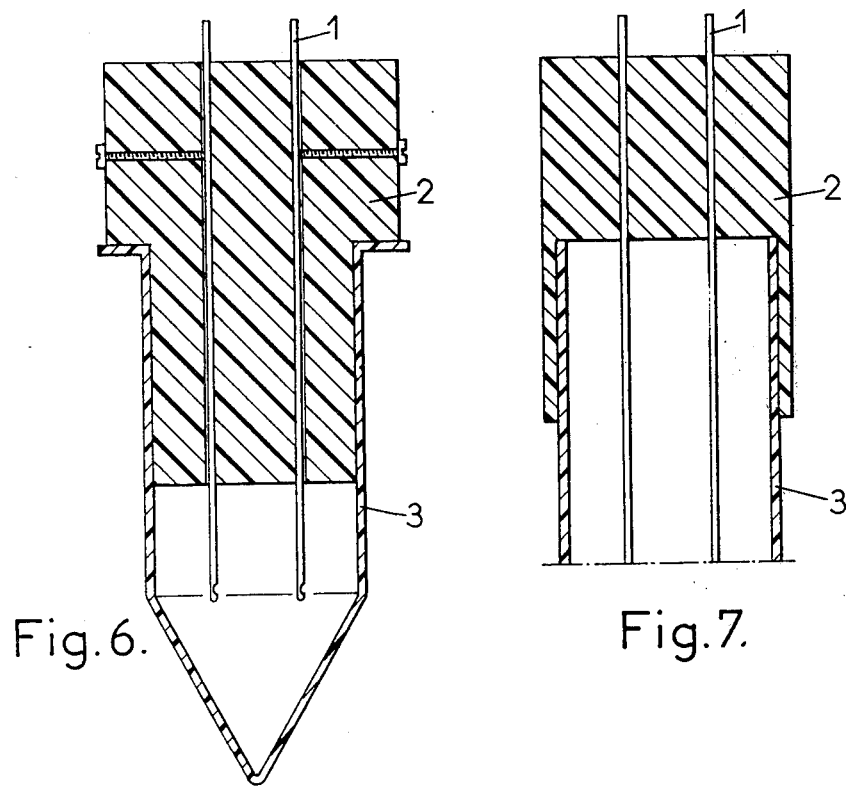
Fig.6. Fig.7.

Fig. 8.
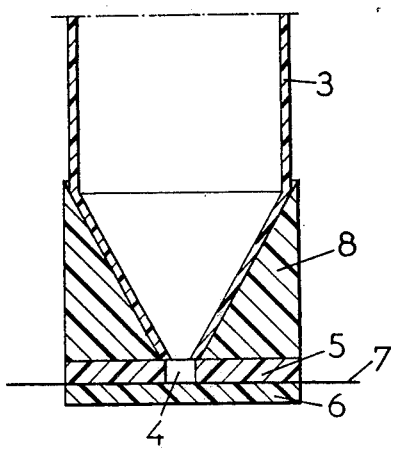
Fig. 9.
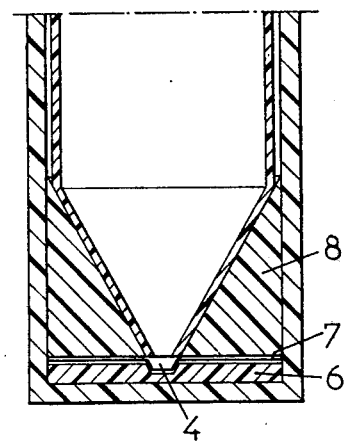
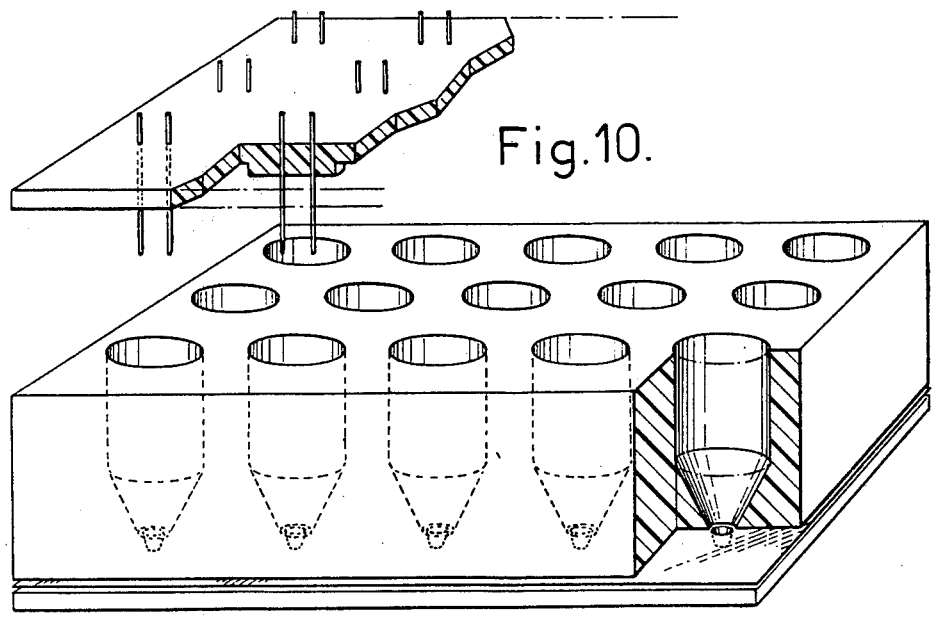
Fig. 10.

MICRO-ANALYSIS PROCESS AND DEVICE

BACKGROUND OF THE INVENTION

The invention relates to novel processes and devices for the analysis of samples of very small volume, which will be referred to hereafter under the general term "micro-analyses".

The practice of analysing very small quantities of a substance is dictated by different considerations. Among these can be mentioned the very high cost of certain reagents and the fact that certain reagents are only available in limited quantities, but the principal reason is in only having very small samples available. These constraints are frequent in the field of biochemical analyses and more particlarly in certain medical diagnosis analyses. A particular field of use of microanalysis techniques is that of enzymatic analysis.

A decisive advantage of the use of very small volumes is the improvement in signal/background noise ratio in the measurement of the observed phenomena. Thus, when an enzymatic reaction is carried out in which the enzymatic activity is very low, the presence of a disporportionate amount of substrate can compromise the measurement. In fact, the substrates used for this type of analysis are never perfectly pure, and the background noise, due to these impurities, makes the signal difficult to read. It is thus desirable, for reactions of this type, to reduce the volume of substrate to quantities comparable with those of the substances to be analysed. Consequently, the background noise is reduced without the signal being modified, which makes the measurement easier and more reliable.

The use of very small amounts of substance in the implementation of the reactions raises particular difficulties connected with the handling of the samples and of the reagents used during these analyses. It is to these that the invention relates.

For the exact measurement of liquid samples of small volume, the instruments principally used at the present time are of the constriction pipette type or microsyringe type. These instruments are however not very convenient in use, even impossible to use when the volumes treated become too small, in particular when the sample or the reagent of measured volume must be constituted as it is, i.e. without being volatilized (as in gas chromatography) or without being introduced into a liquid medium of much larger volume. Thus, under the effect of the electrostatic forces, the droplets of small volume, when they are separated from the instrument which serves to form them, have a tendency to burst spontaneously. The mixture of two droplets, for reacting them, is also a problem, since the forces of cohesion of each of them are opposed to their fusion.

The invention has as its aim to provide a device and process which facilitate the use of reagents and samples in micro-analysis techniques and to improve the accuracy and sensitivity thereof. In particular, the object of the invention is to provide a very accurate measurement of the reacted constituents and to ensure the proper formation of the mixture thereof, so that the reaction can develop normally.

DESCRIPTION OF THE INVENTION

It has in fact been shown that it is possible to remedy these handling difficulties met with previously in the techniques of micro-analysis by means of a device for taking up, measuring out and contacting the constituents of the reaction, e.g. samples to be analysed or reagents, which will be referred to by the general term "reagents", which device comprises:

at least one element for taking up and measuring out a definite amount of the reagent (called hereafter "taking up and measuring out element") a part of which at least is in the form of a rod or a needle; the end of this rod or needle serving for the taking up being arranged so that when it is plunged in, then withdrawn from the reagent, it retains by the action of surface tension, or "capillarity", a definite volume thereof;

a support capable of receiving one or more taking up-measuring out elements, permanently or temporarily fixable on this support;

a container on which said support can be positioned, and possibly fixed, so that the ends of the taking up-measuring out elements carrying the fractions of reagents are inside said container, the cross-section of the container, in the part opposite that on which the support is positioned, being progressively reduced so that the drops of reagent can collect by gravity (centrifugation) at the same point.

To achieve the fixing of a drop of very small volume, by capillarity, at the end of a rod or needle, or else adjacent this end, varied arrangements can be adopted. They are conditioned by the material of the rod, its dimensions, its surface condition, and of course by the nature of the liquid taken, all characteristics on which depend the interactions of the liquid and the needle or the rod.

The end of the rod or needle of the taking-up-measuring out element will be of a dimension and will have a surface condition such that the fixing of the liquid takes place at the position provided therefor and only at this position. This position may be provided in different ways; in some cases, the simple cross-section of the needle may suffice for retaining a droplet whereas, because of the curvature of the needle, the liquid is not retained on the cylindrical parts. It is also possible to provide a cavity, an anfractuosity, or a modification of the surface condition at the end of the rod or needle, or laterally adjacent this end. The purpose of these arrangements is to facilitate the "clinging" of the droplet to the rod or needle. The needle may, in particular, be provided with a lateral opening. Cylindrical needles made from steel or from sufficiently rigid plastic materials (polyamides, polyesters, polytetrafluoroethylene etc.) can be used advantageously.

The taking up-measuring out elements may be fixed on their support in different ways. In particular, the rods or needles may be friction fitted into housings provided therefor in the mass of the support. The needles or rods may also be fitted into channels crossing through the support with locking means (key, pin, screw etc.) being provided for holding them in a fixed position when necessary.

The shape of the support is advantageously such that it is adapted to the container in the manner of a cap or a lid; the positioning of the support on the container may be achieved in particular by partially fitting the support in the container, or conversely. In both cases, a stop position limits the movements of the support in relation to the container. The assembly can also be achieved by screwing the support on to the container, or vice-versa, or else by any other conventional means for carrying out this type of assembly.

Advantageously, the container has the general shape of a tube whose end opposite that which receives the support narrows to form a funnel. This latter may be either closed, in the case where the reaction and the analysis are carried out in the same tube, or open to emerge over a subsidiary receptacle. The opening of the tube, in this case, is limited to the useful dimensions for letting the reagents pass into the receptacle and, in any case, the opening has dimensions at least equal to those of the corresponding receptacle, so that all the reagents are properly channelled towards the receptacle. Advantageously, the device of the invention is thus combined with known receptacles, used for micro-analyses and known as "micro-dishes". These receptacles are formed from sheets of plastic material of small thickness and are generally transparent, thus facilitating the observation of the reaction, particularly for spectrophotometric or spectrofluorimetric measurements. The micro-dishes are advantageously formed by simple pockets formed in the same sheet of polymer material, by stamping for example, they may also be formed from the whole of a flat polymer sheet caught between two plates provided with an opening. In this case, the micro-dish is defined by the sheet forming the bottom and by the opening of one of the plates for the side walls. When such receptacles are used for the implementation of the process of the invention, means are provided for the relative positioning of the tube and the micro-dish, so that the dish is placed opposite the opening of the "funnel".

The assembly formed by the support, the tube and possibly the subsidiary receptacle defines preferably a practically closed space.

The device of the invention may also comprise a multiplicity of tubes with the corresponding supports. This arrangement is particularly desirable for routine analyses in which a great number of manipulations of the same kind can be carried out in series. A particular arrangement consists in moulding or shaping the tubes in a single piece. In this case, to each tube may correspond a distinct support, but advantageously the supports are combined in a single part fitting that forming the tubes. In this case also, the use of micro-dishes is particularly advantageous. For this purpose there can be disposed on the same sheet of plastic material as many micro-dishes as there are tubes, the positioning in relation to each other being carried out in a single operation.

In the processes of the invention which are described further on, the tubes or assemblies of tubes which have just been discussed are subjected to centrifuging. They may then again be provided with means for fixing them in a centrifuge.

The invention will be well understood by referring to the accompanying figures of particular embodiments of devices according to the invention in which:

FIGS. 1 to 5 show schematically an enlargement of some types of end for the rods or needles usable in the devices of the invention;

FIG. 6 is a schematical section of the mounted assembly comprising a support (2) with two needles (1) maintained in position by locking screws, and a tube (3) whose funnel end is closed;

FIG. 7 is a schematical section of another type of tube/support assembly;

FIG. 8 is a schematical section of the open end of the funnel shaped tube (3) and of a receptacle (4) formed by two support plates (5) and (6), one of which has an opening opposite the funnel, a sheet of polymer material (7), imprisoned between the two plates, forms the bottom of the receptacle, a positioning piece (8) maintaining the tube (3) in position;

FIG. 9 is a schematical section of another embodiment of the receptacle (4); a micro-dish is formed in sheet (7) and is housed in a corresponding cavity in plate (6);

FIG. 10 shows in perspective, with a partial section of a tube, an assembly of tubes combined in the same block, the plate bearing the micro-dishes and the supporting piece.

To carry out a micro-analysis according to the invention and with one of the devices having the characteristics which have been described before, the following is offered:

each taking up-measuring out element is dipped in the appropriate reagent, then withdrawn with the droplet taken and retained by capillarity; at this stage, the taking up-measuring out elements are fixed on a support, but they may also be fixed after the droplet has been taken up;

the support is placed on the corresponding container and the whole is subjected to a sufficiently intense centrifuging for the droplets to be detached from the taking up-measuring out elements and to be projected towards the end of the container where they collect, as the case may be, at the bottom of the container or in a receptacle disposed at the open end of this latter. The reaction and the analysis are then continued along the lines and with the means usual in micro-analysis.

The quantities of liquid taken for these micro-analyses are normally less than 1 $\mu l$. They may also be as low as 0.01 $\mu l$ or even less. Most often, the quantities taken are between 0.1 and 1 $\mu l$.

It should be noted that by using the taking up devices of the invention there is obtained, for the same liquid and the same device, a remarkably reproducible volume with a minimum of precaution. Moreover, the relative accuracy is practically independent of the volume considered whereas, with the devices used up to now, the relative error in the volume increases very rapidly with the smallest quantities usable. If it is necessary, the quantity taken in each operation can be accurately determined by a previous calibration of the taking up element used.

The fractions of liquid fixed by capillarity on the rods or needles must be wholly recovered, then combined to form the reactive mixture. We have mentioned the difficulties which normally result from handling very small volumes. By centrifuging, the droplets of liquid are separated without difficulty and are collected in the same receptacle. The centrifugal force exerted must be sufficient to overcome the surface tensions which retain the droplet on the taking up element and especially to overcome the forces of cohesion which are opposed to the joining together of several droplets. For example, centrifugation of the order of 3000 g or more is suitable.

During the different manipulations of these very small volumes, losses by evaporation must be avoided. It is during centrifuging that the risks of evaporation are the greatest. Therefore, to avoid these difficulties, the reagents taken are maintained in a closed space defined by the tube, the support and possibly the receptacle, at least during the centrifuging operation.

When a closed tube is used, the reactive medium is formed at the bottom of the tube and the reaction and the analysis must be continued in the tube, which may present real difficulties taking into consideration the dimensions of the tube in relation to those of this reactive medium. It is therefore preferable to recover this medium in a receptacle whose characteristics facilitate later operations. This is why it is advantageous to use according to the invention a receptacle of the micro-dish type. The volume of the micro-dish may be as small as desired, particularly of the order of a few microliters.

After centrifuging, the micro-dish is separated from the tube to go on with the measurements of the results of the reaction. At this stage, it may be advantageous to enclose and seal the reactive mixture in the micro-dish to avoid any loss. A second sheet of polymer material can then be used to close the micro-dish. This operation is particularly useful when the reaction is not immediate and when a certain time of "incubation" must be observed. This is particularly the case for enzymatic analyses which constitute the most important field of micro-analysis.

The process of the invention which has just been described applies equally in the case where a multiple tube device is used for series analyses. In this case, a single centrifugation is necessary and the assembly of the micro-dishes may, for example, be subjected simultaneously to a uniform incubation treatment. These devices lend themselves also to automated analysis in an appropriate measuring apparatus, particularly in apparatus of the spectrophotometer or spectrofluorimetry type.

Because of their low cost, the micro-dishes are not re-used. Moreover, after centrifuging, no trace of liquid remains attached to the needles or the tubes, so that it is not necessary before re-using the devices, to provide a cleaning or sterilizing operation, which is a definite advantage for routine analyses made in great number.

The devices and processes of the invention are applicable to all analyses which may be carried out on very small volumes of substance. The most important field of application, as has been stated, is that of enzymatic reactions and in particular of diagnosis reactions. In these reactions, the characteristics of the enzymatic activity of an organ, of a tissue etc. are revealed. Micro-analysis is then all the more advantageous as one is led to carry out the measurement on samples corresponding to the enzymatic activity of a very restricted number of cells, even of a single cell. The accuracy of the measurement is tied in fact, to a large extent, to the concentration of the enzyme in the medium analysed. So, for the same enzymatic activity, it is desirable to work with a volume as small as possible so as to limit dilution. Likewise, the quantities of substrate used for these analyses must be as low as possible.

The micro-analysis techniques are useful particularly for carrying out diagnoses, e.g. hepatic or renal diseases, from small quantities of serum, or else blood disorders. They enable also convenient analyses to be made of different internal secretions or of the cephalo-rachidian liquid.

They enable also the detection of frequent genetic illnesses such as mucoviscidose, or rare genetic illnesses such as the gangliosidoses $GM_1$ and $GM_2$ (by the absence of ganglioside-$\beta$-galactosidase), Gaucher's disease and Fabry's disease, as well as the Lesch-Nynan syndrome (due to the deficiency of hypoxanthine-guanine-phosphoryl-transferase), and this from the beginning of pregnancy, by studying for example the cells of the amniotic liquid.

In the laboratory, a micro-analysis in enzymatic measurements is also a very efficient means for genetic complementation studies. These studies serve particularly for detecting genetic heterogeneities, for classifying hereditary diseases, for determining the nature of the proteins occurring in these diseases, In these measurements of enzymatic activity following the methods of micro-analysis, the measurement is advantageously achieved by spectrophotometry, spectrofluorimetry, or else by radioactive counting techniques. These methods present in fact the advantage of being able to be used even when the sample studied is of a very small volume, which is the case by definition when micro-analysis is carried out. Spectrophotometry or spectrofluorimetry may be used each time that the enzymatic reaction is accompanied by the formation or the disappearance of a compound having a particular absorption spectrum. This is the case particularly with numerous hydrolases which release methylumbeliferone from appropriate artificial substrates or from dehydrogenases which reduce the NADP, which become highly fluorescent in the presence of an alkaline solution. When a radioactive substrate is used, after incubation, separation of the constituents is carried out following the usual techniques of chromatography, electrophoresis etc. and the activity of the different constituents of the reactive mixture is measured by counting.

These applications have of course no limiting character; they are given for the sole purpose of indicating the fields in which the processes and devices of the invention are particularly useful.

Although the use of the micro-analysis processes for enzymatic measurement have been specially described, it goes without saying that these latter form only a preferred example.

The invention provides then an improved device and process for facilitating micro-analysis.

I claim:

1. A device for taking up, measuring out and contacting reagents during microanalysis comprising:
   at least one taking up and measuring out element, at least one part of which is in the form of a rod or a needle with an eye provided adjacent its end, the end or lateral side adjacent the end of said rod or needle having a surface portion adapted to retain reagent so that, when inserted into the reagent and withdrawn therefrom, it retains, by surface tension, a definite volume of reagent;
   at least one support capable of having attached thereto said at least one taking up and measuring out element; and
   a container having at least one cavity aligned with said at least one element, so that when the support has the at least one element attached thereto and is positioned on the container, the end of said at least one element carrying the reagent is inside said container, and wherein the cross-section of said container, in the part opposite that on which the support is positioned, is progressively reduced so that the reagent may collect by gravity or centrifugation toward the bottom.

2. The device according to claim 1, wherein said surface portion is an anfractuosity, a perforation or an irregularity.

3. The device according to claim 1, wherein said element is a cylindrical needle provided with an eye adjacent its end.

4. The device according to claim 1, wherein said container is a tube closed at one end forming a funnel.

5. The device according to claim 1, 2 or 3, wherein said container is a tube, one end of which forms a funnel which opens above a receptacle which extends the tube but is distinct therefrom.

6. The device according to claim 5, wherein said receptacle is formed by a micro-dish.

7. The device according to claim 1, wherein the support and container assembly is constructed so that it may be disposed in a centrifuge.

8. The device according to claim 1, wherein said device comprises a plurality of containers combined in a single assembly or formed in a single piece for simultaneously carrying out a series of similar analyses.

9. A micro-analysis process comprising the steps of:
(a) taking up at least one reagent used during the analysis by means of at least one taking up-measuring out element operating by surface tension;
(b) positioning said at least one element inside a container; and
(c) subjecting the element and container assembly to centrifugation of a sufficient intensity for the reagent taken to separate from the element and to be projected to the bottom of the container.

10. The process according to claim 9, wherein the volume of said reagent taken up is less than 1 $\mu$l.

11. The process according to claim 9 or 10, wherein during said centrifugation step (c), to avoid loss of reagent by evaporation, the quantities taken are held in a practically closed space, formed by the container and a support for the taking up-measuring out elements.

12. The process according to claim 9, wherein said container comprises a tube, one end of which forms a funnel above a micro-dish made from a sheet of a polymer material, which micro-dish extends the tube but is distinct therefrom.

13. The process according to claim 9, wherein the reagent is deposited by centrifugation in a receptacle, the bottom of which, coming into contact with the deposit, is a sheet of a polymer material held between two plates and the side walls of which are the internal walls of an opening in a plate disposed between the polymer sheet and the container, said container being a tube forming a funnel, the narrowest end of which is a hole in the container adjacent said opening.

14. The device according to claim 1, wherein said at least one element is permanently attached to said support.

15. The device according to claim 1, wherein said at least one element is removably attached to said support.

16. The device according to claim 1, wherein more than one element is attached to said support and wherein said container comprises a number of cavities equal in number to and in alignment with said elements.

17. The device according to claim 1, said device further comprising a means to limit movement of the support on the container.

18. The device according to claim 1, wherein said definite volume is less than 1 $\mu$l.

19. The device according to claim 6, wherein said micro-dish is formed by a sheet of a polymer material.

20. The device according to claim 5, wherein the support, container and receptacle assembly is constructed so that it may be disposed in a centrifuge.

21. The device according to claim 5, wherein said device comprises a plurality of containers in combination in a single assembly or formed in a single piece for simultaneously carrying out a series of similar analyses.

22. The process according to claim 9, wherein said centrifugation is at 3000 g or more.

23. The process according to claim 9, wherein said container is a tube, one end of which forms a funnel which opens above a receptacle which extends the tube but is distinct therefrom.

24. The process according to claim 9, said at least one element being attached to at least one support.

25. The process according to claim 9, wherein at least a part of said element is in the form of a non-tubular rod or needle, the end or lateral side of said rod or needle having a surface condition whereby, when inserted into the reagent, the surface condition takes up the reagent by surface tension.

26. The process according to claim 12, further comprising the step of
(d) enclosing the reagent on said polymer sheet after step (c) with a second polymer sheet.

27. The process according to claim 13, further comprising the step of
(d) enclosing the reagent on said polymer sheet after step (c) with a second polymer sheet.

28. A device for taking up, measuring out and contacting reagents during microanalysis comprising:
at least one taking up and measuring out element, at least one part of which is in the form of a nontubular rod or a nontubular needle with an eye provided adjacent its end, the end or lateral side adjacent the end of said rod or needle having a surface portion adapted to retain reagent so that, when inserted into the reagent and withdrawn therefrom, it retains, by surface tension, a definite volume of reagent;
at least one support cable of having attached thereto said at least one taking up and measuring out element; and
a container having at least one cavity aligned with said at least one element, so that when the support has the at least one element attached thereto and is positioned on the container, the end of said at least one element carrying the reagent is inside said container, and wherein the cross-section of said container, in the part opposite that on which the support is positioned, is progressively reduced so that the reagent may collect by gravity or centrifugation toward the bottom.

* * * * *